United States Patent
Couillaud

(10) Patent No.: US 10,028,325 B2
(45) Date of Patent: Jul. 17, 2018

(54) MEDICAL COMMUNICATION SYSTEM AND COMMUICATION METHOD

(71) Applicant: Fresenius Vial SAS, Brézins (FR)

(72) Inventor: Frederic Couillaud, Coublevie (FR)

(73) Assignee: Fresenius Vial SAS, Brézins (FR)

( * ) Notice: Subject to any disclaimer, the term of this patent is extended or adjusted under 35 U.S.C. 154(b) by 17 days.

(21) Appl. No.: 15/118,606

(22) PCT Filed: Feb. 19, 2015

(86) PCT No.: PCT/EP2015/053501
§ 371 (c)(1),
(2) Date: Aug. 12, 2016

(87) PCT Pub. No.: WO2015/124670
PCT Pub. Date: Aug. 27, 2015

(65) Prior Publication Data
US 2017/0055308 A1 Feb. 23, 2017

(30) Foreign Application Priority Data
Feb. 20, 2014 (EP) ..................................... 14305232

(51) Int. Cl.
*H04W 76/15* (2018.01)
*H04W 76/14* (2018.01)
(Continued)

(52) U.S. Cl.
CPC ............ *H04W 76/15* (2018.02); *A61M 5/142* (2013.01); *G06F 19/3418* (2013.01);
(Continued)

(58) Field of Classification Search
None
See application file for complete search history.

(56) References Cited

U.S. PATENT DOCUMENTS 6,406,426 B1 6/2002 Reuss et al.
2007/0210917 A1* 9/2007 Collins, Jr. ........... A61B 5/1117
340/539.1
(Continued)

OTHER PUBLICATIONS

Anonymous: "Make Windows 7 ignore WiFi when ethernet is available—Super User" (Dec. 11, 2013).
Anonymous: "Power-line communication—Wikipedia, the free encyclopedia" (Feb, 14, 2014).
Anonymous: "Wireless Limitations—University of Strathclyde" (Jun. 22, 2012).
Evans: "Wired vs wireless in the enterprise", Computer Weekly, 9 (Mar. 1, 2013).
(Continued)

*Primary Examiner* — Mohammad Adhami
(74) *Attorney, Agent, or Firm* — Cook Alex Ltd.

(57) ABSTRACT

The invention relates to a medical communication system, comprising at least one medical device (2a, 2b, 2c); a gateway (31) configured for establishing at least one wireless link to an access point; wherein the medical device (2a, 2b, 2c) comprises a unit (22a, 22b, 22c) for establishing a communication connection to the gateway (31) and a unit (21a, 21b, 21c) for establishing a direct wireless link to the access point, and wherein the medical device (2a, 2b, 2c) is configured to detect whether or not a communication connection to the gateway (3) is established and to set up a direct wireless communication link to the access point if a communication connection to the gateway (31) is not established, wherein the medical communication system is configured to set up a communication link between the medical device (2a, 2b, 2c) and the access point via the gateway (31) if a communication connection between the medical device (2a, 2b, 2c) and the gateway (31) is established.

13 Claims, 1 Drawing Sheet

(51) Int. Cl.
*H04W 4/80* (2018.01)
*G06F 19/00* (2018.01)
*A61M 5/142* (2006.01)
*H04B 3/54* (2006.01)
*H04W 84/12* (2009.01)
*H04W 88/08* (2009.01)
*H04W 88/16* (2009.01)

(52) U.S. Cl.
CPC ............ *G06F 19/3468* (2013.01); *H04B 3/54* (2013.01); *H04W 4/80* (2018.02); *H04W 76/14* (2018.02); *A61M 2205/3584* (2013.01); *H04W 84/12* (2013.01); *H04W 88/08* (2013.01); *H04W 88/16* (2013.01)

(56) References Cited

U.S. PATENT DOCUMENTS

| 2011/0035627 A1* | 2/2011 | Jeon | G06F 19/322 714/25 |
| 2016/0180046 A1* | 6/2016 | Sezeur | G06F 3/017 700/90 |

OTHER PUBLICATIONS

International Search Report and Written Opinion, counterpart PCT Appl. No. PCT/EP2015/053501 (dated May 11, 2015).

Mckinney, "Disadvantages of Wireless Networks / eHow" (Oct. 9, 2013).

* cited by examiner

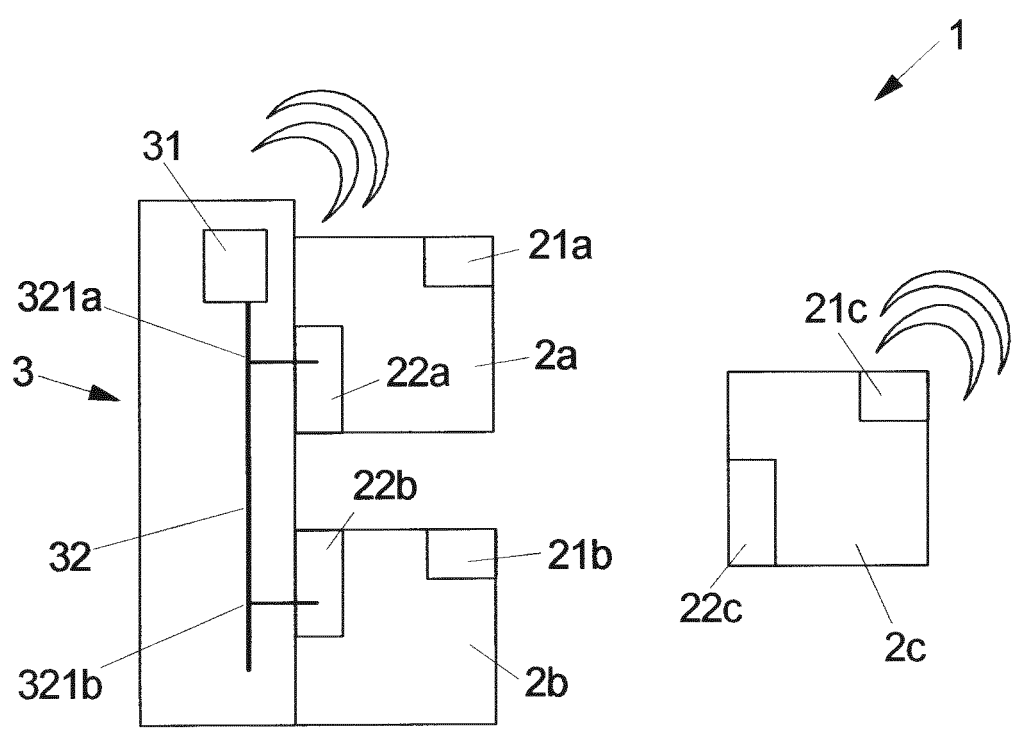

MEDICAL COMMUNICATION SYSTEM AND COMMUICATION METHOD

The present application is a U.S. National Stage of PCT International Patent Application No. PCT/EP2015/053501, filed Feb. 19, 2015, which claims priority to EP Application No. 14305232.2, filed Feb. 20, 2014, both of which are hereby incorporated herein by reference.

BACKGROUND

The invention relates to a medical communication system and a communication method.

It is known in the art to equip medical devices such as medical pumps (e.g. infusion pumps) with wireless communication capabilities permitting the medical devices to communicate with a network (such as a hospital network) via a wireless communication link (using, for example, the Wi-Fi standard). The wireless communication link to the network in particular is established via an access point of the network, wherein the medical devices located in the range (the region of coverage) of the access point will connect to the access point. An example of a medical communication system using wireless communication links is described in U.S. Pat. No. 6,406,426 B1.

However, an access point can only support a limited number of connections (e.g. 128), wherein this number may not be sufficient to allow all medical devices within the range of the access point to connect to the access point while maintaining an acceptable quality of service level.

It is an object of the invention to allow multiple medical devices to connect to an access point for wireless communication while maintaining the quality of service level.

SUMMARY

According to the invention, a medical communication system is provided, comprising
at least one medical device;
at least one gateway configured for establishing at least one wireless link to an access point;
wherein the medical device comprises a unit for establishing a communication connection to the gateway and a unit for establishing a direct wireless link to the access point;
and wherein the medical device is configured to detect whether or not a communication connection to the gateway is established and to set up a direct wireless link to the access point if a communication connection to the gateway is not established, wherein the medical communication system is configured to set up a communication link between the medical device and the access point via the gateway if a communication connection between the medical device and the gateway is established.

The medical communication system may comprise a communication line connected to the gateway, wherein the unit for establishing a communication connection to the gateway is configured for establishing a communication connection to the gateway via the communication line. That is, the medical device will establish a communication link to the gateway via the communication line if it is connected to the communication line and will refrain from establishing a direct, individual wireless link to the access point. Thus, a plurality of medical devices connected to the communication line will establish a wireless communication link to the access point via the gateway instead of using direct individual wireless connections, thereby reducing the number of individual wireless connections that have to be supported by the access point.

The communication line may be a backbone line, i.e. a core communication line of the medical communication system, e.g. a core communication line of a telecommunication network. For example, the medical communication system comprises a backbone line arrangement (such as a backbone network), e.g. of a hospital network, wherein the gateway and the backbone line are part of the backbone line arrangement or form the backbone line arrangement. The backbone line arrangement (in particular the backbone line) may be part of a larger network. Further, the medical communication system might also comprise a separate device which allows mounting one or more medical devices, especially medical pumps, and connecting them to the communication line (for example, the backbone line of the backbone line arrangement), e.g. in a certain kind of order (spatial arrangement), like vertically or horizontally.

The gateway may comprise at least one wireless communication module (e.g. a Wi-Fi module) for establishing a wireless link to the access point, which e.g. forms part of a communication network such as a hospital communication network. The gateway of the backbone may also be configured for establishing a wired connection to a network such that a wired link between the medical device and the network may be realized. Also, the medical device may be configured for establishing a direct wired link to a network (such as a hospital network).

The backbone line arrangement may also be configured for supplying electrical power to the medical device, wherein the link between the medical device and the wireless communication module over the backbone line arrangement may be realized by a separate communication line (e.g. a communication bus) arranged in addition to a power line of the backbone line arrangement. However, it is also conceivable that the link between the medical device and the wireless communication module of the gateway is establish via the power line of the backbone line arrangement (using PLC power line communication technology).

Further, the medical device's unit for establishing a communication connection to the gateway may be configured to establish a wired electrical or optical communication connection to the gateway. For example, the medical communication system comprises at least one communication port to which the unit for establishing a communication connection to the gateway of at least one medical device is connected (e.g. via a cable), wherein the link between the communication port and the wireless communication module of the gateway may be realized by a communication line or a power line of a backbone line arrangement as previously discussed.

The invention also relates to a communication method, in particular using a medical communication system as described above, comprising the steps of:
providing a gateway configured for establishing at least one wireless link to an access point;
providing at least one medical device, wherein the medical device comprises a unit for establishing a communication connection to the gateway and a unit for establishing a direct wireless link to the access point; and
detecting whether or not a communication connection to the gateway is established;
and setting up a direct wireless communication link between the medical device and the access point if a communication connection to the gateway is not established, or setting up a communication link between the medical device and the access point via the gateway if a communication connection between the medical device and the gateway is established.

BRIEF DESCRIPTION OF THE DRAWINGS

An embodiment of the invention is described hereinafter with reference to the FIGURE.

DETAILED DESCRIPTION OF THE EMBODIMENTS

The FIGURE schematically shows a medical communication system 1 according to the invention, the system comprising a plurality of medical devices in the form of medical pumps, in this embodiment infusion pumps 2a-c.

Each one of the infusion pumps 2a-c comprises a unit in the form of a Wi-Fi module 21a-c for establishing a direct wireless link to an access point (not shown) of a hospital communication network. The Wi-Fi modules 21a-c permit each one of the infusion pumps 2a-c to establish an individual wireless communication link to the hospital network's access point.

Two of the infusion pumps (pumps 2a and 2b) are connected to a backbone line arrangement 3, wherein the backbone line arrangement 3 supplies electrical power to the infusion pumps 2a, 2c. Moreover, the backbone line arrangement 3 comprises a non-Wi-Fi to Wi-Fi gateway 31 including a Wi-Fi module for establishing a wireless link between the backbone line arrangement 3 and the access point of the hospital network. The gateway 31 is connected to a communication line (backbone line) in the form of a communication bus 32 of the backbone line arrangement 3.

Further, each one of the infusion pumps 2a-c comprises a unit in the form of interfaces 22a-c for establishing a wired communication connection to a communication port 321a, 321b of the communication bus 32 of the backbone line arrangement 3. Thus, the infusion pumps 2a-c may communicate with the Wi-Fi module of the gateway 31 and thus with the access point of the hospital network via the communication bus 32 of the backbone line arrangement 3, wherein the communication via the communication bus 32 will be used instead of an individual, direct Wi-Fi link to the access point. In the embodiment of the FIGURE, only pumps 2a, 2b are connected to the communication bus 32 of the backbone line arrangement 3 and thus to the gateway 31 such that these will use the gateway 31 for wireless communication with the access point.

Only pump 2c, which is not connected to the backbone line arrangement 3, will establish a direct Wi-Fi link to the access point. Using the gateway 31 of the backbone line arrangement 3 a plurality of medical devices may be connected via a single Wi-Fi unit (the one of the gateway 31) such that the number of Wi-Fi connections that must be supported by the access point is reduced. It is noted that instead of a wired connection between the pumps 2a, 2b and the communication ports 321a, 321b of the backbone line arrangement 3 a wireless link or an optical connection may be used.

Of course, more than three pumps may be provided, wherein more than two pumps can be connected to the communication bus 32. Further, the communication bus 32 may comprise more than two communication ports 321a, 321b such that more than one pump may be connected to the communication bus 32. It is also conceivable that several medical devices (such as the pumps 2a, 2b) are connected in parallel to one communication port 321a, 321b.

Thus, a high number of infusion pumps (or other medical devices) may be connected to the gateway 31 and thus to the access point of the hospital network via the communication bus 32. For example, if 10 pumps are assigned to each one of the beds of an intensive care unit and more than 10 beds are located in the intensive care unit, more than 100 devices may be linked to the access point via the backbone line arrangement 3. Thus, the number of direct wireless connections that must be supported by the access point may be significantly reduced, thereby avoiding a saturation of the access point and maintaining a high quality of service level.

It is noted that gateway 31 may comprise more than one Wi-Fi module, wherein each one of the Wi-Fi modules may be assigned to one of the communication ports 321a, 321b such that the group of pumps connected to the one of the communication ports 321a, 321b may be assigned to one of the gateway's Wi-Fi modules.

However, the gateway 31 may also comprise a single Wi-Fi module only which is assigned to all pumps connected to the backbone line arrangement 3.

The infusion pumps 2a-c are furthermore configured to detect whether or not a communication connection to the gateway 31 via the backbone line arrangement 3 is established and to set up a direct wireless link to the access point if a communication connection to the gateway 31 is not established. In the embodiment illustrated in the FIGURE, the infusion pumps 2a and 2b are connected to the backbone line arrangement 3 and thus to gateway 31 such that these pumps will communicate with the hospital's network access point via the Wi-Fi module of the gateway 31 instead of using a direct Wi-Fi link to the access point by means of their Wi-Fi modules 21a, 21b. The Wi-Fi modules 21a, 21b of infusion pumps 2a, 2b thus may be deactivated.

However, infusion pump 2c is not connected to the gateway 31 as there is no connection to the backbone line arrangement 3 (pump 2c may be about to be moved together with a patient it is assigned to). In this case, the pump detects that it is not connected to the backbone line arrangement 3 and establishes an individual, direct Wi-Fi connection to the access point via its integrated Wi-Fi module 21c (indicated by the curved wave front lines). For example, as soon as it is unplugged from the communication bus 32 of the backbone line arrangement 3 the pump 2c activates its Wi-Fi module 21c for connecting to the access point in order to maintain the communication connection with the pump. If pump 2c was connected to the communication bus 32 of the backbone line arrangement 3 again, its Wi-Fi module 21c may be disabled and a Wi-Fi connection via the Wi-Fi module of gateway 31 will be used instead.

It is noted the embodiment shown in the FIGURE is only exemplarily. Other configurations of the medical communication system may be used. For example, at least some of the medical devices connected to the hospital's network via a Wi-Fi link (directly or via the gateway 31) are not, although preferred, medical pumps, but other medical devices such as e.g. monitoring devices.

REFERENCE SIGNS 1 medical communication system
2a, 2b, 2c infusion pump
3 backbone line arrangement
21a, 21b, 21c Wi-Fi module
22a, 22b, 22c interface
31 gateway
32 communication bus
321a, 321b communication port

The invention claimed is:

1. A medical communication system, comprising:
   a plurality of medical devices;
   a gateway configured for establishing at least one wireless link to an access point;
   wherein each one of the medical devices comprises a unit for establishing a communication connection to the gateway and a unit for establishing a direct wireless link to the access point; and
   a communication line connected to the gateway, wherein the unit for establishing a communication connection to the gateway is configured to establish a communication connection to the gateway via the communication line and the communication line is a communication bus,
   and wherein the medical devices are configured to detect whether or not a communication connection to the gateway via the communication line is established and to set up a direct wireless communication link to the access point if a communication connection to the gateway via the communication line is not established, wherein the medical communication system is configured to set up a communication link between the medical devices and the access point via the communication line and the gateway if a communication connection between the medical devices and the gateway is established via the communication line.

2. The medical communication system as claimed in claim 1, wherein the communication line is a backbone line.

3. The medical communication system as claimed in claim 2, further comprising a backbone line arrangement comprising the gateway and the backbone line.

4. The medical communication system as claimed in claim 3, wherein the backbone line arrangement is configured for supplying electrical power to the medical device.

5. The medical communication system as claimed in claim 1, wherein the plurality of medical devices is connected to the communication line and a communication link between the medical devices and the access point is established via the communication line and the gateway.

6. The medical communication system as claimed in claim 1, wherein the unit for establishing a communication connection to the gateway is configured to establish a wired electrical or optical communication connection to the gateway.

7. The medical communication system as claimed in claim 1, wherein the unit for establishing a communication connection to the gateway is configured to establish a wireless communication connection to the gateway.

8. The medical communication system as claimed in claim 1, wherein the communication line comprises a plurality of communication ports, wherein to each one of the communication ports a plurality of medical devices is assigned.

9. The medical communication system as claimed in claim 1, further comprising a device for mounting one or more medical devices and connecting them to the communication line.

10. The medical communication system as claimed in claim 1, wherein the gateway comprises at least one Wi-Fi module for establishing the at least one wireless link to the access point.

11. The medical communication system as claimed in claim 1, wherein the gateway is a non-Wi-Fi to Wi-Fi gateway.

12. The medical communication system as claimed in claim 1, wherein the medical device is a medical pump.

13. Communication method, in particular using a medical communication system according to claim 1, comprising the steps of:
   providing the gateway configured for establishing at least one wireless link to an access point;
   providing the plurality of medical devices, wherein each one of the medical devices comprises the unit for establishing a communication connection to the gateway and the unit for establishing a direct wireless link to the access point, and the communication line connected to the gateway, wherein the units for establishing the communication connection to the gateway are configured to establish the communication connection to the gateway via that communication line and wherein the communication line is the communication bus; and
   detecting whether or not a communication connection to the gateway is established via the communication line; and
   setting up a direct wireless communication link between the medical devices and the access point if a communication connection between the medical devices and the gateway via the communication line is not established or setting up a communication link between the medical devices and the access point via the communication line and the gateway if a communication connection between the medical devices and the gateway is established via the communication line.

* * * * *